United States Patent
Pickhard

(10) Patent No.: US 8,105,293 B2
(45) Date of Patent: Jan. 31, 2012

(54) INJECTION SYRINGE

(75) Inventor: Ewald Pickhard, Grossebersdorf (AT)

(73) Assignee: Pharma Consult Ges.m.b.H & Co Nfg KG (AT)

( * ) Notice: Subject to any disclaimer, the term of this patent is extended or adjusted under 35 U.S.C. 154(b) by 0 days.

(21) Appl. No.: 12/226,099

(22) PCT Filed: Apr. 4, 2007

(86) PCT No.: PCT/AT2007/000153
§ 371 (c)(1),
(2), (4) Date: Jun. 22, 2009

(87) PCT Pub. No.: WO2007/112470
PCT Pub. Date: Oct. 11, 2007

(65) Prior Publication Data
US 2009/0312703 A1 Dec. 17, 2009

(30) Foreign Application Priority Data
Apr. 6, 2006 (AT) .................................. A589/2006

(51) Int. Cl.
*A61M 5/32* (2006.01)
(52) U.S. Cl. ........ 604/199; 604/110; 604/187; 604/192; 604/216; 604/240; 604/243; 604/246; 604/195
(58) Field of Classification Search .................. 604/110, 604/187, 192, 218, 240, 241, 243, 263, 195, 604/199
See application file for complete search history.

(56) References Cited

U.S. PATENT DOCUMENTS

| | | | | |
|---|---|---|---|---|
| 4,888,002 A | * | 12/1989 | Braginetz et al. | 604/195 |
| 4,969,884 A | * | 11/1990 | Yum | 604/892.1 |
| 5,205,824 A | * | 4/1993 | Mazur | 604/110 |
| 5,256,151 A | | 10/1993 | Chul et al. | |
| 5,263,934 A | | 11/1993 | Haak | |
| 5,370,619 A | | 12/1994 | Rossi et al. | |

(Continued)

FOREIGN PATENT DOCUMENTS

CA 2537056 * 3/2005

(Continued)

*Primary Examiner* — Nicholas D Lucchesi
*Assistant Examiner* — Leah Stohr
(74) *Attorney, Agent, or Firm* — Lerner, David, Littenberg, Krumholz & Mentlik, LLP

(57) ABSTRACT

The syringe is intended for one-off use and has a syringe barrel (1), a barrel stopper (12) which can be displaced in the syringe barrel (1) by means of a plunger rod (11) and a needle unit (25) accommodated in the syringe barrel (1). The plunger rod (11) and the needle unit (25) are connected to one another by coupling means (20, 40) in order to retract the needle unit (25) into the syringe barrel (1) after the injection. As proposed by the invention, the needle unit (25) comprises a needle holder (26) made from plastic surrounding an injection needle (27) made from stainless steel along part of its length, which is closed off from an interior of the syringe barrel (1) containing an injection solution (50) by means of a seal insert (36) made from pharmaceutical rubber through the injection needle (27) extends from the rear end. As a result of this feature, an injection solution (50) contained in the syringe is in contact exclusively with permitted materials and the syringe can therefore be stored pre-filled.

18 Claims, 5 Drawing Sheets

U.S. PATENT DOCUMENTS

| | | | | |
|---|---|---|---|---|
| 5,584,817 | A | * | 12/1996 | van den Haak ............... 604/195 |
| 5,593,391 | A | * | 1/1997 | Stanners ........................ 604/232 |
| 5,968,019 | A | | 10/1999 | Lee |
| 5,997,512 | A | | 12/1999 | Shaw |
| 6,059,756 | A | | 5/2000 | Yeh et al. |
| 6,193,687 | B1 | | 2/2001 | Lo |
| 6,248,094 | B1 | | 6/2001 | Epperson |
| 6,344,031 | B1 | | 2/2002 | Novacek et al. |
| 6,423,033 | B1 | | 7/2002 | Tsai |
| 6,613,016 | B1 | | 9/2003 | Ku et al. |
| 2005/0277880 | A1 | | 12/2005 | Shue et al. |

FOREIGN PATENT DOCUMENTS

| | | |
|---|---|---|
| DE | 298 21 609 U1 | 1/1999 |
| EP | 1 514 566 A1 | 3/2005 |
| WO | WO-91/08788 A1 | 6/1991 |

* cited by examiner

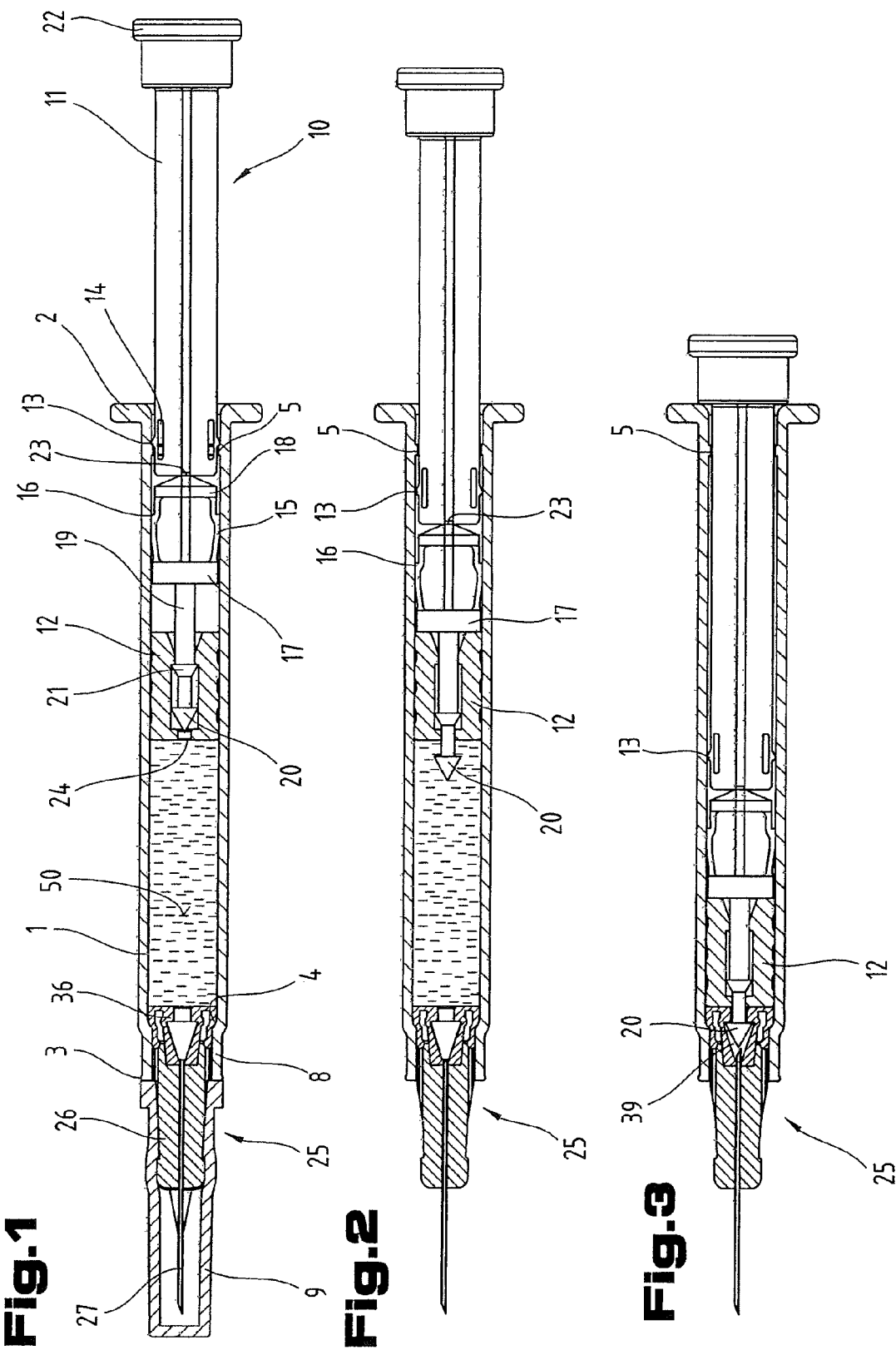

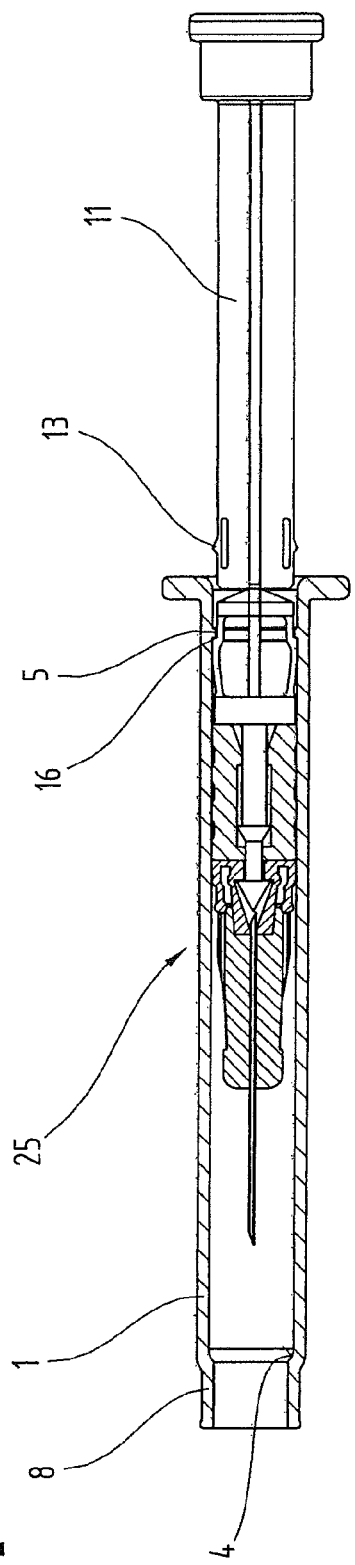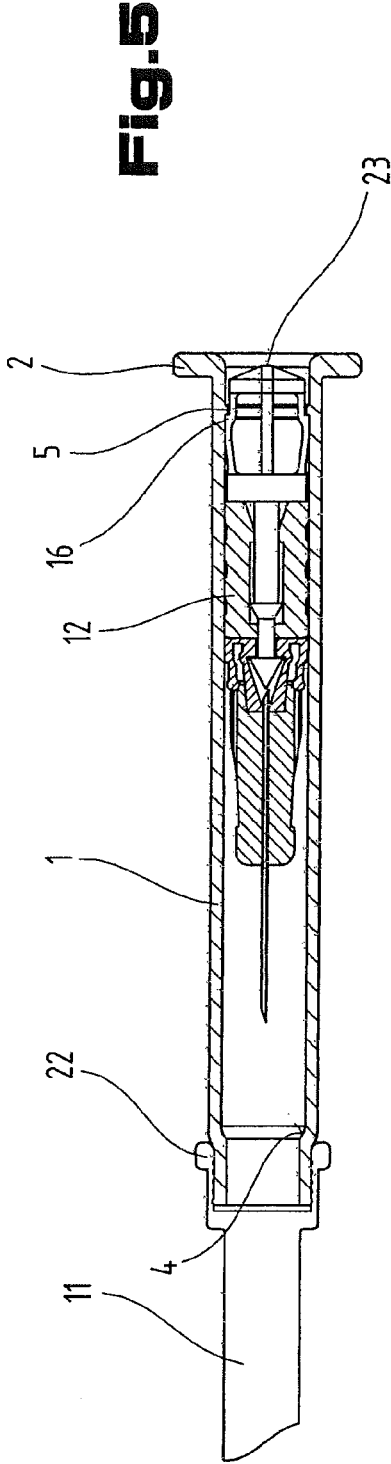

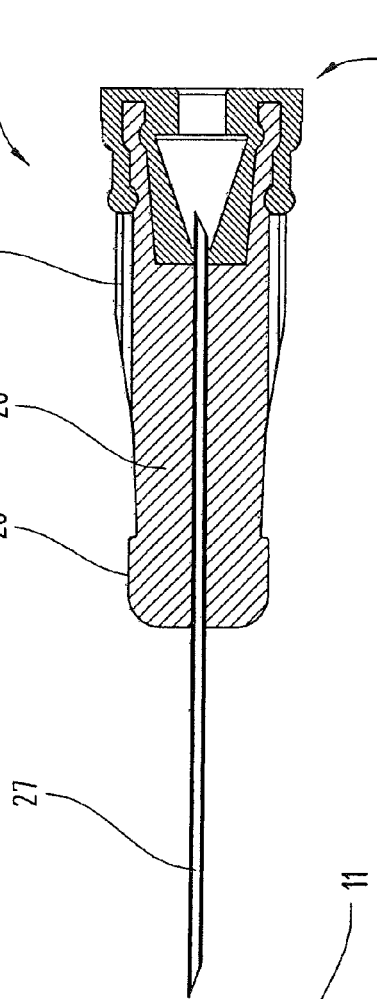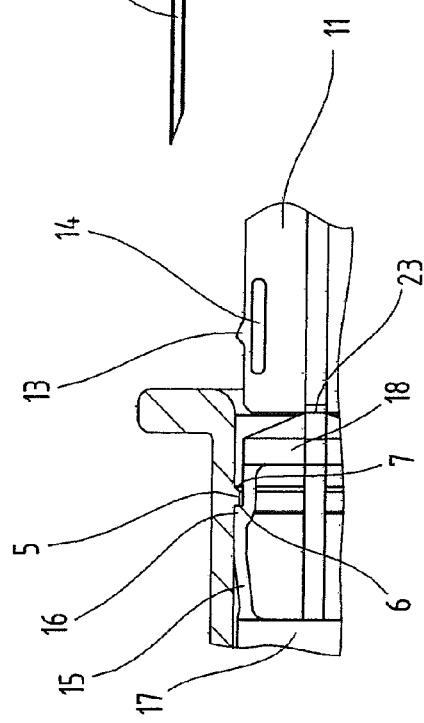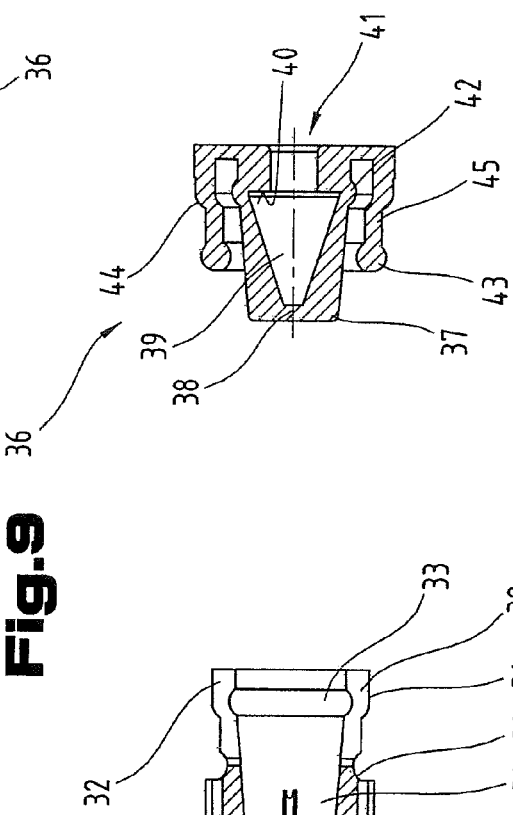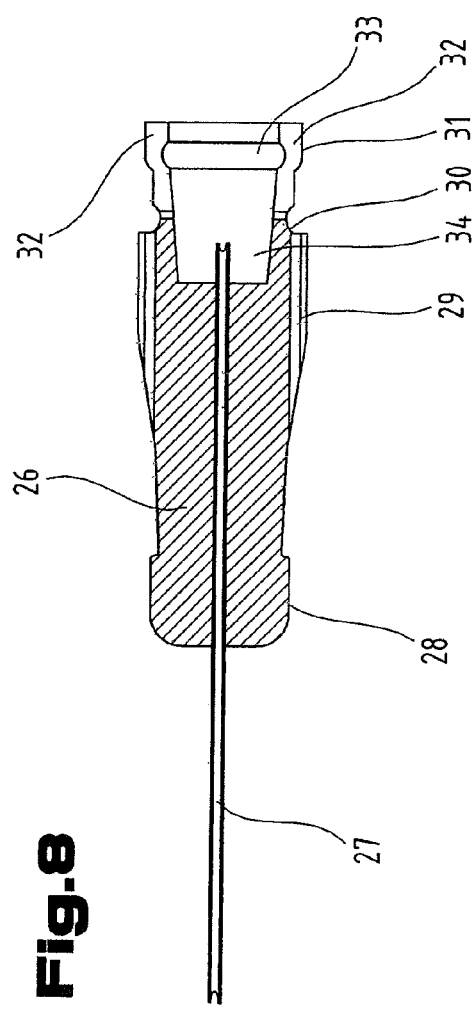

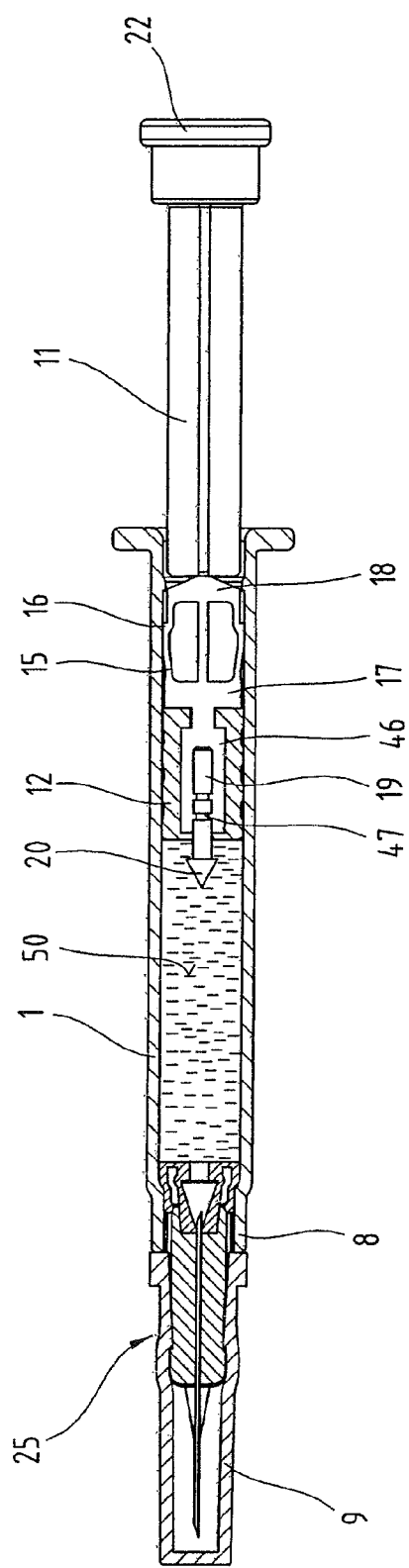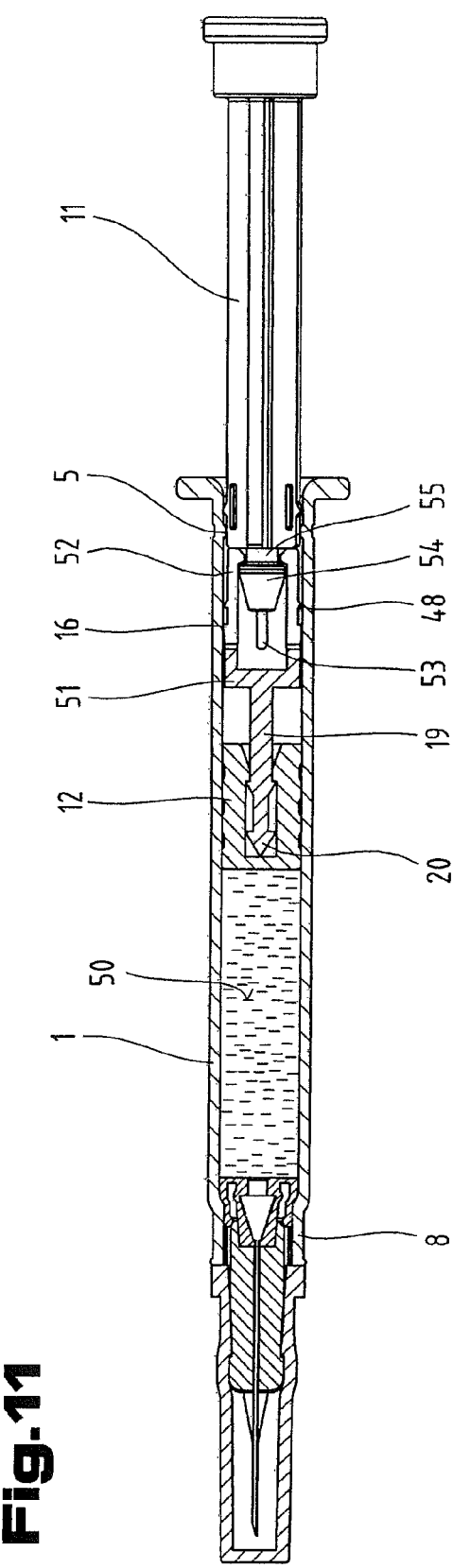

INJECTION SYRINGE

The invention relates to a syringe for one-off use, with a syringe barrel, a barrel stopper which can be displaced in the syringe barrel by means of a plunger rod, a needle unit accommodated in the syringe barrel and coupling means for connecting the plunger rod to the needle unit so that the needle unit is retracted into the syringe barrel once the injection has been administered.

Syringes of the type whereby the needle is retracted into syringe barrel once the injection has been administered in order to prevent injuries by the injection needle and prevent the syringe from being used again are known in many designs, such as that disclosed in document U.S. Pat. No. 6,613,016 B1 for example. As long as the injection solution is primed shortly before the intended injection when using such syringes, there is no problem as regards the choice of material. However, there are currently only three known materials which are permitted for long-term contact with an injection solution. These are glass, pharmaceutical rubber and stainless steel. As a result of this restriction with regard to the choice of material, constructive problems occur with specific syringes intended for one-off use which are supplied pre-filled and where the needle is retracted into the syringe barrel after the injection because the plastics commonly used for all types of disposable articles which can be processed by injection casting must not come into contact with the injection solution during storage of the syringe.

Against the background of this prior art, the objective of the invention is to propose a syringe of the type outlined above in which the injection solution sits in contact exclusively with the above-mentioned, currently permitted materials during storage.

This objective is achieved by the invention due to the fact that the needle unit has a needle holder made from plastic surrounding an injection needle of stainless steel across a part of its length, which is closed off from the region of the interior of syringe barrel containing the injection solution by means of a seal insert made from pharmaceutical rubber through which the injection needle extends from the rear end.

The advantage gained as a result of the features defined in the characterizing part of claim 1 specifically resides in the fact that in spite of using plastic for the needle holder, the injection solution does not come into contact with materials that are not permitted whilst the syringe is being stored. Another advantage of this inventive solution is the fact that the syringe is simple and inexpensive to manufacture and assemble, which is particularly important in the case of an item that is to be used once only.

Also of advantage is another embodiment defined in claim 2, whereby the needle holder has a head with a wider diameter at its injection end, on which a needle guard cap can be fitted. As a result of this feature, the diameter of the needle guard cap can be kept smaller than if the needle guard cap were designed to be fitted on the syringe barrel.

Also of advantage is an embodiment defined in claim 3, whereby the needle holder is provided with longitudinal ribs on a region of its external face by means of which it is accommodated in the narrowed end region of the syringe. Since the syringe barrel is preferably made from glass and can therefore not be manufactured within very tight tolerances, these ribs take up any extra dimension there might be because they deform slightly as the needle holder is inserted in the syringe barrel.

The embodiment defined in claim 4 is characterized by the fact that the needle holder has a cut-out at its end remote from the injection end through which the end of the injection needle remote from the injection end extends, the advantage of which is that the requirements are fulfilled for producing a pre-assembled needle unit.

In another embodiment defined in claim 5, at least one slot extending essentially axially is provided in the wall of the needle holder surrounding the cut-out. This imparts radial elasticity to the relevant region for accommodating the coupling means of the plunger rod.

Another type of embodiment is defined in claim 6, whereby the seal insert extends by means of an extension into the cut-out of the needle holder and surrounds the external face of the needle holder in the region of the cut-out by means of a collar. As a result, the seal insert is retained on the needle holder on the one hand and a sealing of the needle unit in the syringe barrel is assured on the other hand.

In another type of embodiment defined in claim 7, the seal insert has an annular bead in the end region of its extension remote from the injection end, which locates in an annular groove disposed in the internal wall, thereby enabling the seal insert to latch with the needle holder.

In the embodiment defined in claim 8, the seal insert has a sealing bead on its collar, which on the one hand locates in an annular groove disposed on the needle holder and on the other hand lies against the internal wall of the syringe barrel affording a seal, thereby sealing it off from bacteria. This results in a reliable sealing of the needle unit, irrespective of fluctuations in tolerances of the diameter of the syringe barrel.

If a shoulder is formed on the external circumference of the seal insert by means of which the seal insert lies axially against a shoulder disposed in the injection-end region of the syringe barrel, as is the case with the embodiment defined in claim 9, axial forces expended on the needle during the injection are optimally absorbed.

As a result of the embodiment defined in claim 10, the needle unit can be reliably coupled with the plunger rod after the injection because a cavity is provided in the seal insert from which an opening extends forming an annular collar to the interior of the syringe barrel, and the rear end of the injection needle extends into this cavity.

In the case of another type of embodiment defined in claim 11, an inner annular bead is provided close to the end of the syringe barrel remote from the injection end, the front face of which directed towards the injections end is oriented at least approximately at a right angle to the wall of the syringe barrel and the rear face of which remote from the injection end subtends an obtuse angle with the wall of the syringe barrel. This results in a positioning means which acts as a latching aid when the plunger rod is being assembled and serves as a stop when the plunger rod is retracted.

In another type of embodiment defined in claim 12, stop cams are provided on the plunger rod, with a face remote from the injection end oriented essentially at a right angle to the longitudinal axis of the plunger rod which sits against the front face of the inner annular bead directed towards the injection end when the plunger rod is retracted, thereby making it impossible for the plunger rod to be pulled completely out of the syringe barrel.

The embodiment defined in claim 13 is distinctive due to the fact that catch cams are provided on the plunger rod at a distance from the stop cams at the end remote from the injection end, the faces of which are designed so that the catch cams can be moved past the inner annular bead of the syringe barrel by overcoming a resistance in both directions.

In the embodiment defined in claim 14, the plunger rod has cut-outs in the region of the catch cams so that the catch cams are able to flex radially, which means that said resistance can be kept so low that no damage occurs as it is overcome.

Another embodiment defined in claim 15 is distinctive because a breaking point is provided on the plunger rod in a region between the stop cams and the catch cams. As a result, once the injection has taken place and the plunger rod together with the needle unit coupled with it has been retracted, the part of the plunger rod extending out of the syringe barrel can be broken off, which reliably prevents the syringe from being used again.

In an alternative embodiment defined in claim 16, the plunger rod comprises two parts, which are releasably connected to one another by other coupling means, and the coupling means are designed so that they can be released exclusively in an operating position in which the plunger rod has been retracted as far as a stop. This means that when the injection has taken place and the plunger rod together with the needle unit coupled with it has been retracted, the part of the plunger rod projecting out from the syringe barrel can be uncoupled, thereby reliably preventing the syringe from being used again.

A special type of embodiment is defined in claim 17, whereby the coupling means contains a coupling sleeve connected to the plunger stopper on which coupling claws are formed remote from the injection end, which locate round a coupling head, and the coupling head can then only be released by the radially resilient, flexible retaining claws if they are disposed with at least a part of their length outside of the syringe barrel or in an end region of the syringe barrel with a larger diameter. As a result, the coupled plunger rod together with the needle unit coupled with it can be reliably retracted as far as an end stop after the injection before the part of the plunger rod which is then extending out from the syringe barrel is uncoupled as described above.

Finally, in the case of another embodiment defined in claim 18, a terminal sleeve is disposed on the rear end of the plunger rod remote from the injection end, the rearwardly directed opening of which has a diameter which matches that of the front end of the syringe barrel. Accordingly, the syringe can be tightly closed again after use.

An example of an embodiment of the invention will be described in more detail with reference to the appended drawings.

Of these:

FIG. 1 shows a pre-filled syringe for one-off use in the initial position;

FIG. 2 shows the syringe in injection-ready mode;

FIG. 3 shows the syringe after the injection;

FIG. 4 shows the syringe with the injection needle retracted;

FIG. 5 shows the syringe in a locked state, ready for disposal;

FIG. 6 shows a detail from FIG. 4 on a larger scale;

FIG. 7 shows the needle unit of the syringe illustrated in FIGS. 1 to 6;

FIG. 8 shows the needle holder including the injection needle of the needle unit illustrated in FIG. 7;

FIG. 9 shows the seal insert of the needle unit illustrated in FIG. 7;

FIG. 10 shows another type of embodiment of the syringe in the initial position;

FIG. 11 shows another type of embodiment of the syringe in the initial position;

Figure 12:
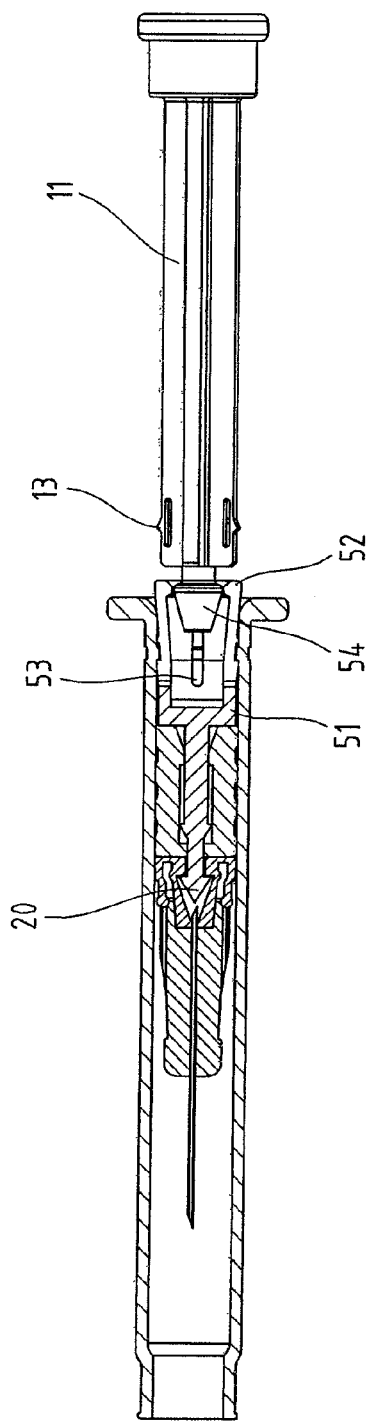
FIG. 12 shows the syringe illustrated in FIG. 11 after the injection and FIG. 13 shows a detail from FIG. 12 on a larger scale.

Firstly, it should be pointed out that the same parts described in the different embodiments are denoted by the same reference numbers and the same component names and the disclosures made throughout the description can be transposed in terms of meaning to same parts bearing the same reference numbers or same component names. Furthermore, the positions chosen for the purposes of the description, such as top, bottom, side, etc., relate to the drawing specifically being described and can be transposed in terms of meaning to a new position when another position is being described.

FIGS. 1 to 5 illustrated five steps involved in using one embodiment of the syringe proposed by the invention, which is primarily a pre-fillable syringe for one-off use.

A syringe barrel 1 made from glass has a flange 2 on its rear end as viewed in the injection direction, which serves as a support for the finger of a person using the syringe during the injection. In this description, the term "front" is generally used to refer to the injection end and the term "rear" is used to refer to the end of the syringe remote from the injection needle. At its front end, the syringe barrel 1 has a neck 8 which has a narrower diameter than it, on which at least one locking bead 3 is formed, the purpose of which will be explained below. Disposed in the interior of the syringe barrel 1 at the transition to the neck 8 is a shoulder 4. Disposed in the interior of the syringe barrel 1 close to its rear end is an annular bead 5. As may be seen from the detail illustrated on a larger scale in FIG. 6, this annular bead has a front face 6 oriented essentially at a right angle to the internal wall of the syringe barrel 1 and a rear face 7 which subtends an obtuse angle with the internal wall of the syringe barrel 1. Accommodated in the front end of the syringe barrel 1 is a needle unit 25, reference 25 denoting it as a whole, which will be described in more detail below, on which a needle guard cap 9 sits in the operating position illustrated in FIG. 1.

Inserted in the rear end of the syringe barrel 1 is a plunger unit 10 denoted as a whole by reference 10, which in turn comprises a plunger rod 11 extending out from the syringe barrel 1 in the operating position illustrated in FIG. 1 and a plunger stopper 12 sitting on its front end. As illustrated, the plunger rod 11 preferably comprises two webs crossing at a right angle, at least one of which bears a catch cam 13 which sits against the annular bead 5 in the operating position illustrated in FIG. 1 and thus affords a resistance to the movement of the plunger rod 11 in the injection direction. To enable the catch cam 13 to flex radially inwards, a cut-out 14 is provided underneath it in the web. Disposed in front of the catch cam or cams 13 on the plunger rod 11 is a breaking point 23 and adjoining it at the front a rear plate 18 and a front plate 17. The webs are cut in the region between these plates so as to form outwardly lying resilient webs 15 which flex radially inwards, on which stop cams 16 extending radially outwards are formed. In the projection on the front end of the front plate 17, the plunger rod 11 has a preferably cylindrical shaft 19, bearing a radially projecting shoulder 21 and finally an arrow-shaped tip 20 at the end. In the region of the tip 20, the plunger stopper 12 is closed in a sealed arrangement by means of a membrane 24 integrally formed on it. At the rear end, the plunger rod 11 is terminated by a terminal sleeve 22 open towards the rear.

The needle unit 25 mentioned above is illustrated more accurately in FIGS. 7 to 9 on a larger scale than in FIGS. 1 to 5. An injection needle 27 of stainless steel is enclosed by a plastic needle holder 26. This combination of injection needle 27 and needle holder 26 illustrated in a longitudinal section in FIG. 8 is produced by injecting around the needle in an injection casting machine. At the front end, the needle holder 26 has a head 28 with a wider diameter, on which the needle guard cap 9 sits in the operating position illustrated in FIG. 1. At the end remote from the head 28, the needle holder has longitudinal ribs 29 on its external circumference, which compensate for any unavoidable tolerances occurring during manufacture when the needle unit 25 is accommodated in the neck 8 of the syringe barrel 1. Adjoining the longitudinal ribs 29, an annular groove 30 is formed in the needle holder 26 and adjacent to it is a collar 31. Starting from the rear end of the needle holder 26, two slots 32 are provided, offset from one another by 180°, which extend into the region of the annular groove 30. These slots 32 are only visible in FIG. 8 because the needle holder 26 in FIG. 7 is rotated about the longitudinal axis by 90° compared with the diagram of FIG. 8. An approximately frustoconical cut-out 34 extends from the rear end of the needle holder 26 through the latter and coaxially with it, and the rear end of the injection needle 27 extends into this cut-out, as clearly illustrated in FIG. 8. An inner annular groove 33 is formed in this cut-out 34.

A seal insert 36 is fitted on the rear end of the needle holder 26, as illustrated in FIG. 9. It has an extension 37 which fits in the cut-out 34, which is surrounded by a circumferentially extending collar 45. Disposed in the interior of the seal insert 36 is a wedge-shaped cavity 39, with a cylindrical orifice 41 extending back from it forming an annular collar 40. Disposed in the region of the tip of the conical cut-out 39, a weakening 38 is provided in the wall of the seal insert, through which the injection needle 26 extends from the rear end when the seal insert 36 is mounted on the needle holder 26. FIG. 7 illustrates the assembled state in which the rear end of the injection needle 27 extends through the conical cut-out 39 of the seal insert 36. An annular bead 42 disposed on the rear end of the extension 37 locates in the inner annular groove 33 of the needle holder 26 when the seal insert 36 is fitted and secures and positions the seal insert 36 in the needle holder 26. A sealing bead 43 is provided on the front end of the collar 45, which seals the needle unit 25 in the syringe barrel 1 in the same way as an O-ring, keeping it free of bacteria. Disposed at a distance from the sealing bead 43 is a shoulder 44, which sits against the shoulder 4 of the syringe barrel when the needle unit 24 is fitted in the syringe barrel 1, thereby forming a stop.

As a result of the construction described above, the injection solution 50 contained in the syringe is not in contact with plastic or any other non-permitted substance for any length of time during the initial state illustrated in FIG. 1. The seal insert 36 sealing the needle unit 25 off from the interior of the syringe barrel 1 is made from pharmaceutical rubber, which is in contact with the injection needle 27 of stainless steel, as mentioned above, extending through the seal insert 36, and is therefore also in contact with the injection solution 50.

The plunger stopper 12 sealing the syringe barrel 1 at the rear is also made from pharmaceutical rubber and the syringe barrel 1 is made from glass, as explained above. A stainless steel suitable for the application described here is the material known as Niro 1.43.01, for example. A so-called pharmaceutical rubber is the material known as FM 257/2, for example.

In order to assemble the syringe, the pre-assembled needle unit 25 is firstly introduced into the syringe barrel 1 from the rear and pushed forward until the shoulder 44 of the seal insert 36 sits against the shoulder 4. The needle guard cap 9 is then fitted on the needle holder 26 and, in order to seal the needle tip, it is of advantage if the needle tip pierces the end wall of the needle guard cap 9 to the degree that the subsequently introduced injection solution 50 is prevented from escaping. The syringe is therefore sealed to prevent ingress by bacteria at the injection end. The injection solution 50 is then introduced and the plunger stopper 12 is pushed into the syringe barrel 1 as far as the position illustrated in FIGS. 1 and 2. The plunger rod 11 is then pushed in so that the catch cams 13 sitting against the annular bead 5 prevent the plunger rod 11 from being pushed so far that the tip 20 penetrates the membrane 24 of the plunger stopper.

The way the syringe is operated is as follows. From the initial position illustrated in FIG. 1, the needle guard cap 9 is removed first of all, the syringe is vented and the injection needle 27 is inserted in the skin or tissue of a person.

In the operating position illustrated in FIG. 2, the plunger rod 11 has been moved forwards, but the plunger stopper 12 initially remains in its position in the syringe barrel 1, against which it is firmly retained due to friction and the pressure of the incompressible injection solution 50. Once the resistance caused by the catch cams 13 and annular bead 5 has been overcome, the plunger rod 11 can be pushed forwards so that the tip 20 of the plunger rod 11 made from plastic is able to pierce the membrane 24 of the plunger stopper 12, and the rebounding material of the plunger stopper 12 sits in a sealing arrangement against the shaft and thus prevents the injection solution from escaping at the rear. The contact of the tip 20 with the injection solution up to the instant at which is has been fully dispensed lasts for only a few seconds as a rule. As may be seen from FIG. 4, the front plate 17 now sits against the rear end of the plunger stopper 12 and pushes it forwards during the remaining movement of the plunger rod in the syringe barrel 1 and ejects the injection solution 50 through the injection needle 27.

In the operating position illustrated in FIG. 3, the injection solution has been fully dispensed and the tip 20 of the plunger rod 11 has penetrated the cut-out 39 in the seal insert of the 36 needle unit 25. This penetrating movement is made possible or facilitated due to the fact that the rear end of the needle holder 26 can be radially stretched due to the slots 32.

From the operating position illustrated in FIG. 3, the entire syringe is firstly pulled back so that the tip of the injection needle 27 moves out of the person's skin. The plunger rod is then retracted by reference to the syringe barrel 1 so that the annular collar 40 prevents the tip 20 from moving out of the cut-out 39 again. Consequently, the entire needle unit 25 is pulled backwards into the syringe barrel. Since both faces of the catch cams 13 directed towards the front and to the rear subtend an obtuse angle with the plunger rod 11, the catch cams 13 are forced inwards by the annular bead 5 and are not able to move past it. This retracting movement terminates on reaching an end position illustrated in FIG. 4, when the rear faces of the stop cams 16 sit essentially on the annular bead 5 at a right angle to the longitudinal axis. The plunger rod 11 is then broken off, which is facilitated by the breaking point 23. The broken-off end of the plunger rod 11 can be fitted on the neck 8 of the syringe barrel 1 by means of the terminal sleeve 22 and is retained in this position on the locking bead 3 of the syringe barrel by circumferentially extending grooves. The injection needle 27 is therefore completely enclosed and protected against contact. Naturally, in kinematic terms, a cylindrical pin (not illustrated in the drawings) may also be provided on the rear end of the plunger rod 11 which can be fitted in the neck 8 of the syringe barrel 1 once the rear part of the plunger rod has been broken off.

FIG. 10 illustrates an example of another embodiment of the syringe proposed by the invention. By contrast with the example illustrated in FIGS. 1 to 5, the tip 20 extends out from the plunger stopper 12 in the initial position already in this example and is thus in contact with the injection solution 50. This necessarily means that the tip 20 must be made from a permitted material. In this particular example, this is a stainless steel of the type mentioned above. As may be seen from FIG. 10, the tip 20 together with its shaft is cast in a housing barrel 46, and the shaft 19 integrated by injecting into the housing barrel 46 so that it is in turn integrally formed with the plunger rod 11. The shaft 19 is therefore firmly anchored in the housing barrel 46 and the tensile forces which occur when the plunger rod 11 is retracted do not cause the shaft 19 to come apart from the housing barrel 46, and annular grooves 47 are provided in the shaft 19 which are filled with plastic when the housing barrel 46 is being cast by an injection process. The clearance which may be seen in FIG. 1 between the plunger stopper 12 and the front plate 17 in the operating position in the case of the embodiment described as a first example does not exist in the example illustrated in FIG. 10 and, when the syringe is being assembled, the entire plunger unit comprising the plunger rod 11, the stainless steel shaft 19 inserted in it and the plunger stopper 12 fitted on the latter can be introduced after filling with the injection solution 50.

Figure 13:
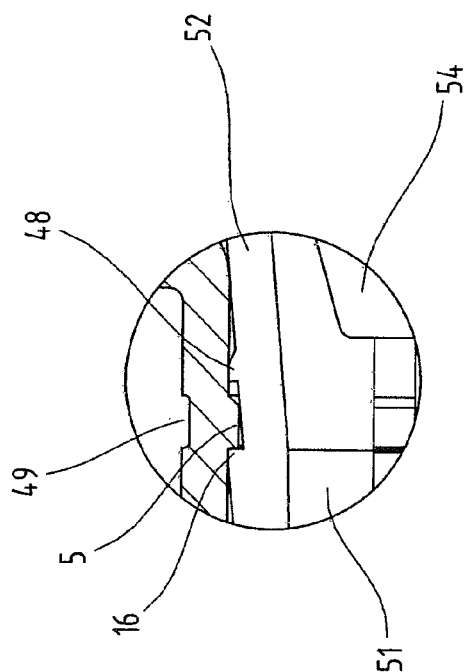

FIGS. 11 to 13 illustrate another example of an embodiment of the syringe, where the plunger stopper 12, shaft 19 and tip 20 are the same as those described in connection with the example of an embodiment illustrated in FIGS. 1 to 5. The example illustrated in FIGS. 11 to 13 differs from the example described above due to the fact that the plunger rod does not have a breaking point 23 but is of a two-part design.

Integrally formed on the rear end of the shaft 19 is a coupling sleeve 51, the wall of which has several cuts 53 open at the rear end of the coupling sleeve 51, thereby forming retaining claws 52 which assume the function of the resilient webs 15 described above on the one hand and enable the two parts of the plunger rod to be separated once the plunger rod 11 together with the needle unit 25 coupled with it has been retracted, as described below. A coupling head 54 is formed on the rear part of the plunger rod 11, which extends into the coupling sleeve 51, where it is axially secured due to the retaining claws 52 which locate in an undercut 55 disposed behind the coupling head 54. As a result, once the injection has taken place, the plunger rod 11 and the needle unit 25 can be retracted. As long as the coupling sleeve 51 is in the syringe barrel 1, the retaining claws 52 are not able to flex radially far enough to enable the coupling head 54 to be released. It is not until the coupling sleeve has assumed the position illustrated in FIG. 12 and at least the free ends of the retaining claws 52 have moved out of the syringe barrel 1 that the retaining claws 52 are able to flex far enough radially outwards to allow the coupling head 54 to be released. Shortly before assuming this position, it is necessary for a positioning bead 48 disposed on the outside of the retaining claws 52 to move past the annular bead and, although this means that the retracting movement briefly comes up against increased resistance, this position can ultimately be reached due to the shape of the positioning bead 48 illustrated in FIG. 13 and due to the retaining claws flexing radially inwards.

In the rear end position illustrated in FIG. 12, the stop cams 16 sit against the inner annular bead 5, as clearly illustrated in the diagram shown on a larger scale in FIG. 13. Once the plunger rod 11 has been broken off, the positioning bead 48 co-operating with the inner annular bead 5 prevents the needle unit 25 with the coupling sleeve 51 from being pushed back into the syringe barrel. Again in this example, the broken-off part of the plunger rod 11 can be fitted on the neck 8 of the syringe barrel 1 by means of the terminal sleeve 22 in order to close it off and prevent injuries which might otherwise be caused by the injection needle 27 and prevent any residues of injection solution 50 from dripping out.

The embodiments illustrated as examples represent possible design variants of the syringe, and it should be pointed out at this stage that the invention is not specifically limited to the design variants specifically illustrated, and instead the individual design variants may be used in different combinations with one another and these possible variations lie within the reach of the person skilled in this technical field given the disclosed technical teaching. Accordingly, all conceivable design variants which can be obtained by combining individual details of the variants described and illustrated are possible and fall within the scope of the invention.

For the sake of good order, finally, it should be pointed out that, in order to provide a clearer understanding of the structure of the syringe, it and its constituent parts are illustrated to a certain extent out of scale and/or on an enlarged scale and/or on a reduced scale.

The objective underlying the independent inventive solutions may be found in the description.

Above all, the individual embodiments of the subject matter illustrated in FIGS. 1 to 9; 10; 11; 12, 13 constitute independent solutions proposed by the invention in their own right. The objectives and associated solutions proposed by the invention may be found in the detailed descriptions of these drawings.

LIST OF REFERENCE NUMBERS

1 Syringe barrel
2 Flange
3 Locking bead
4 Shoulder
5 Annular bead
6 Front face
7 Rear face
8 Neck
9 Needle guard cap
10 Plunger unit
11 Plunger rod
12 Plunger stopper
13 Catch cam
14 Cut-out
15 Resilient web
16 Stop cam
17 Front plate
18 Rear plate
19 Shaft
20 Tip
21 Shoulder
22 Terminal sleeve
23 Breaking point
24 Membrane
25 Needle unit
26 Needle holder
27 Injection needle
28 Head
29 Longitudinal ribs
30 Annular groove
31 Collar
32 Slot
33 Annular groove
34 Cut-out
35
36 Seal insert
37 Extension
38 Weakening
39 Cavity
40 Annular collar
41 Orifice
42 Annular bead
43 Sealing bead
44 Shoulder
45 Collar
46 Housing barrel 47 Annular groove
48 Positioning bead
49 Neck
50 Injection solution
51 Coupling sleeve
52 Retaining claws
53 Cuts
54 Coupling head
55 Undercut

The invention claimed is:

1. Syringe for one-off use, with a syringe barrel having an interior for containing an injection solution, a barrel stopper which can be displaced in the syringe barrel by a plunger rod, a needle unit accommodated in the syringe barrel and coupling means for connecting the plunger rod to the needle unit in order to retract the needle unit into the syringe barrel after injection, characterised in that the needle unit has a needle holder made from plastic surrounding an injection needle made from stainless steel across a part of its length, wherein the needle holder has an end facing the interior of the syringe barrel and wherein a seal insert seals the end of the needle holder from the interior of the syringe barrel, the seal insert being made from pharmaceutical rubber and through which the injection needle extends from a rear end of the needle holder,
wherein the needle holder at an injection end has a head of a wider diameter than a portion of the needle holder adjoining the injection end and on which a needle guard cap can be fitted.

2. Syringe according to claim 1, wherein the needle holder is provided with longitudinal ribs in a region of its external face by means of which it is accommodated in a narrower end region of the syringe barrel.

3. Syringe according to claim 1, wherein the needle holder has a cut-out in its end face, the end face being remote from an injection end of the needle holder, through which an end of the injection needle remote from an injection end extends.

4. Syringe according to claim 3, wherein at least one essentially axially extending slot is provided in a wall of the needle holder surrounding the cut-out.

5. Syringe according to claim 3, wherein the seal insert projects into the cut-out of the needle holder by means of an extension and surrounds the end face of the needle holder in a region of the cut-out by means of a collar.

6. Syringe according to claim 5, wherein the seal insert has a sealing bead on its collar, which locates in an annular groove disposed in the needle holder and lies in a sealing arrangement against an internal wall of the syringe barrel, thereby sealing the needle unit off from bacteria.

7. Syringe according to claim 3, wherein the seal insert has an annular bead in an end region of an extension remote from the injection end, which locates in an annular groove provided in an internal wall of the cut-out.

8. Syringe according to claim 1, wherein a cavity is provided in the seal insert, from which an orifice extends as far as the interior of the syringe barrel forming an annular collar, and a rear end of the injection needle extends through this cavity.

9. Syringe according to claim 1, wherein the plunger rod comprises two parts which are releasably connected to one another by other coupling means and the other coupling means are designed to be released exclusively in an operating position in which the plunger rod has been retracted as far as a stop.

10. Syringe according to claim 9, wherein the other coupling means contain a coupling sleeve connected to the plunger stopper on which coupling claws are formed remote from an injection end, which locate behind a coupling head, and the coupling head can only be released by the radially flexible retaining claws when the claws are disposed with at least a part of their length outside the syringe barrel or in an end region of the syringe barrel with a larger diameter than the claws.

11. Syringe according to claim 1, wherein a terminal sleeve is disposed on an end of the plunger rod remote from an injection end, a rearwardly oriented orifice of which has a diameter matching a front end of the syringe barrel.

12. Syringe for one-off use, with a syringe barrel having an interior for containing an injection solution, a barrel stopper which can be displaced in the syringe barrel by a plunger rod, a needle unit accommodated in the syringe barrel and coupling means for connecting the plunger rod to the needle unit in order to retract the needle unit into the syringe barrel after injection, characterised in that the needle unit has a needle holder made from plastic surrounding an injection needle made from stainless steel across a part of its length, wherein the needle holder has an end facing the interior of the syringe barrel and wherein a seal insert seals the end of the needle holder from the interior of the syringe barrel, the seal insert being made from pharmaceutical rubber and through which the injection needle extends from a rear end of the needle holder,
wherein a shoulder is formed on an external circumference of the seal insert, by means of which the seal insert sits axially against a shoulder of the syringe barrel disposed at an injection-end region of the syringe barrel.

13. Syringe for one-off use, with a syringe barrel having an interior for containing an injection solution, a barrel stopper which can be displaced in the syringe barrel by a plunger rod, a needle unit accommodated in the syringe barrel and coupling means for connecting the plunger rod to the needle unit in order to retract the needle unit into the syringe barrel after injection, characterised in that the needle unit has a needle holder made from plastic surrounding an injection needle made from stainless steel across a part of its length, wherein the needle holder has an end facing the interior of the syringe barrel and wherein a seal insert seals the end of the needle holder from the interior of the syringe barrel, the seal insert being made from pharmaceutical rubber and through which the injection needle extends from a rear end of the needle holder,
wherein an inner annular bead is disposed close to an end of the syringe barrel remote from an injection end, a front face of which directed towards the injection end is oriented at least approximately at a right angle with respect to a wall of the syringe barrel and a rear face of which remote from the injection end subtends an obtuse angle with the wall of the syringe barrel.

14. Syringe according to claim 13, wherein stop cams are provided on the plunger rod, which have a face remote from the injection end oriented essentially at a right angle to the longitudinal axis of the plunger rod, which sit against the front face of the inner annular bead directed towards the injection end when the plunger rod is retracted such that the plunger rod cannot be pulled completely out of the syringe barrel.

15. Syringe according to claim 14, wherein catch cams are provided on the plunger rod at a distance from the stop cams at the end remote from the injection end, the faces of which are designed so that the catch cams can be moved past the inner annular bead of the syringe barrel by overcoming a resistance in both directions.

16. Syringe according to claim 15, wherein the plunger rod has cut-outs in a region of the catch cams, thereby enabling the catch cams to flex radially.

17. Syringe according to claim 14, wherein a breaking point is provided on the plunger rod in a region between the stop cams and the catch cams.

18. Syringe for one-off use, with a syringe barrel having an interior for containing an injection solution, a barrel stopper which can be displaced in the syringe barrel by a plunger rod, a needle unit accommodated in the syringe barrel and coupling means for connecting the plunger rod to the needle unit in order to retract the needle unit into the syringe barrel after injection, characterised in that the needle unit has a needle holder made from plastic surrounding an injection needle made from stainless steel across a part of its length, wherein the needle holder has an end facing the interior of the syringe barrel and wherein a seal insert seals the end of the needle holder from the interior of the syringe barrel, the seal insert being made from pharmaceutical rubber and through which the injection needle extends from a rear end of the needle holder, wherein the needle holder is provided with longitudinal ribs in a region of its external face by means of which it is accommodated in a narrower end region of the syringe barrel.

* * * * *